(12) United States Patent
Burger et al.

(10) Patent No.: US 9,089,514 B2
(45) Date of Patent: Jul. 28, 2015

(54) COMPOSITION AND METHOD FOR INHIBITING BIOGENIC SULFIDE GENERATION

(75) Inventors: Edward D. Burger, Dallas, TX (US); Celia D. Youngren, Plano, TX (US)

(73) Assignee: Arkion Life Sciences, New Castle, DE (US)

( * ) Notice: Subject to any disclaimer, the term of this patent is extended or adjusted under 35 U.S.C. 154(b) by 567 days.

(21) Appl. No.: 12/862,332

(22) Filed: Aug. 24, 2010

(65) Prior Publication Data

US 2012/0053154 A1   Mar. 1, 2012

(51) Int. Cl.
*A01N 57/00* (2006.01)
*A61K 31/60* (2006.01)
*A01N 35/00* (2006.01)
*A61K 31/12* (2006.01)
*A61K 31/66* (2006.01)
*A61K 45/06* (2006.01)

(52) U.S. Cl.
CPC ............... *A61K 31/12* (2013.01); *A61K 31/66* (2013.01); *A61K 45/06* (2013.01)

(58) Field of Classification Search
USPC ................................................. 514/126, 680
See application file for complete search history.

(56) References Cited

U.S. PATENT DOCUMENTS

| 5,728,898 A | 3/1998 | Krackov |
| 5,750,743 A | 5/1998 | Suganuma |
| 5,753,180 A | 5/1998 | Burger |
| 6,309,597 B1 * | 10/2001 | Ballinger et al. ............... 422/28 |
| 2005/0238729 A1 * | 10/2005 | Jenneman et al. ............ 424/617 |
| 2010/0190666 A1 | 7/2010 | Ali et al. |
| 2012/0034313 A1 * | 2/2012 | Wrangham et al. .......... 424/607 |

OTHER PUBLICATIONS

Burger et. al. (Society of Petroleum Engineers International Symposium on Oilfield Chemistry, Houston, TX (2007) pp. 1-8).*
Burger, Ed D., et al. "Flexible Treatment Program for Controlling H2S in FPSO Produced-Water Tanks", Society of Petroleum Engineers International Symposium on Oilfield Chemistry, Houston, TX, Feb. 28-Mar. 2, 2007, pp. 1-8.
Burger et al., "Inhibition of Sulfate-Reducing Bacteria by Anthraquinone in a Laboratory Biofilm Column Under Dynamic Conditions", Presented at NACE International Corrosion, 2001, Paper #01274.

* cited by examiner

*Primary Examiner* — Marcos Sznaidman
(74) *Attorney, Agent, or Firm* — McCarter & English

(57) ABSTRACT

Compositions and methods for inhibiting sulfide biogeneration from biofilms are described, as well as methods for preparing the compositions. The compositions comprise anthrahydroquinone and a biocide. The compositions may also include anthraquinone.

9 Claims, 2 Drawing Sheets

COMPOSITION AND METHOD FOR INHIBITING BIOGENIC SULFIDE GENERATION

FIELD OF THE INVENTION

The invention relates to compositions and methods for inhibiting sulfide biogeneration in biofilms.

BACKGROUND OF THE INVENTION

Uncontrolled microbial growth and activity can create severe environmental and human safety problems in wastewater treatment and handling systems associated with municipal, industrial and oilfield operations. Problems caused or intensified by microbial growth and activity include corrosion, solids production, and hydrogen sulfide ($H_2S$) generation. Hydrogen sulfide not only has a highly offensive odor, but is toxic even in very small concentrations.

The microorganisms primarily responsible for $H_2S$ generation in an anaerobic environment are sulfate-reducing bacteria. These organisms are ubiquitous and can grow in almost any environment. They are routinely found in waters associated with oil production systems and can be found in virtually all industrial aqueous processes, including cooling water systems, pulp and paper-making systems, chemical manufacturing, and petroleum refining.

Hydrogen sulfide is corrosive and reacts with metal surfaces to form insoluble iron sulfide corrosion products. In oilfield operations, $H_2S$ partitions into the water, oil and natural gas phases of produced fluids and creates a number of problems. For instance, oil and gas, which contain high levels of $H_2S$, have a lower commercial value than low sulfide oil and gas. Removing biogenic $H_2S$ from sour oil and gas increases the cost of these products. Hydrogen sulfide is an extremely toxic gas and can be lethal to humans at even small concentrations, and poses a threat to worker safety. In addition, the discharge of produced waters containing high levels of $H_2S$ into aquatic or marine environments lowers the dissolved oxygen levels in the water as $H_2S$ reacts with oxygen.

Corrosion caused by sulfate-reducing bacteria and $H_2S$ frequently results in extensive damage. Pipe systems, tank bottoms and other pieces of equipment can rapidly fail if they have areas where microbial corrosion is occurring. If a failure occurs in a pipeline or storage tank bottom, the released fluid can have serious environmental consequences. If a failure occurs in a high pressure water or gas line, the consequences may be worker injury or death. Any such failure involves substantial repair or replacement costs.

Conditions in an oil reservoir subject to seawater flooding are excellent for establishing sulfate-reducing bacteria activity. Conditions within industrial water systems, such as effluent streams from production operations or cooling water streams, are also conducive to sulfate-reducing bacteria activity due to the anaerobic biofilm which is formed on pipeline, tank or vessel walls. The same is true within the sewers and other piping and to facilities associated with municipal wastewater handling systems.

Tanks used to store produced water on floating production, storage, and offloading units (FPSO) are extremely susceptible to generation of high hydrogen sulfide levels because of the activity of sulfate-reducing bacteria. FSPOs and floating storage and offloading units (FSO) are ships containing multiple tanks for separating oil and water, storing oil before offloading into tankers, and processing waters. Produced water typically flows into slop tanks, where it may also combine with drainage water from decks or ballast water from cargo ships. Slop tanks are in many cases the final separation stage in which residual entrained oil is removed from the water before its discharge to the sea, offloading, or re-injection. Environmental conditions in the slop-water tanks, especially the presence of sludge and solids deposits at the bottom of the tanks, are quite favorable for sulfate-reducing bacteria to form biofilms. These solids are also protective to the bacteria and impede the action of chemical biocide treatments for controlling bioactivity. Health, safety, and environmental aspects associated with the presence of the toxic gas on offshore structures make it necessary to implement effective sulfate-reducing bacteria- and $H_2S$-control procedures while still maintaining compliant water for discharge.

SUMMARY OF THE INVENTION

The invention provides compositions for inhibiting sulfide biogeneration from biofilms. An embodiment of the compositions comprises a solution of anthrahydroquinone and a biocide, wherein the pH of the biocide is less than or equal to about 7, and the pH of the composition is less than about 9. Another embodiment of the compositions comprises a slurry comprising anthrahydroquinone.

The invention further provides methods for preparing the compositions, one such method comprising the steps of a) preparing an aqueous solution of anthrahydroquinone dialkali salt; b) reducing the pH of the solution of step a) to less than about 10; and c) adding the biocide to the solution of step b). Another such method comprises the steps of a) chemically reducing a suspension of anthraquinone to a solution of anthrahydroquinone-dialkali salt having a pH greater than or equal to about 13; and b) reducing the pH of the solution of step a) to less than or equal to about 10, wherein the solution forms a slurry.

The invention also provides a method for inhibiting sulfide biogeneration from biofilms, the method comprising adding the compositions of the invention to vessels or conduits.

DETAILED DESCRIPTION OF THE INVENTION

Figure 1:
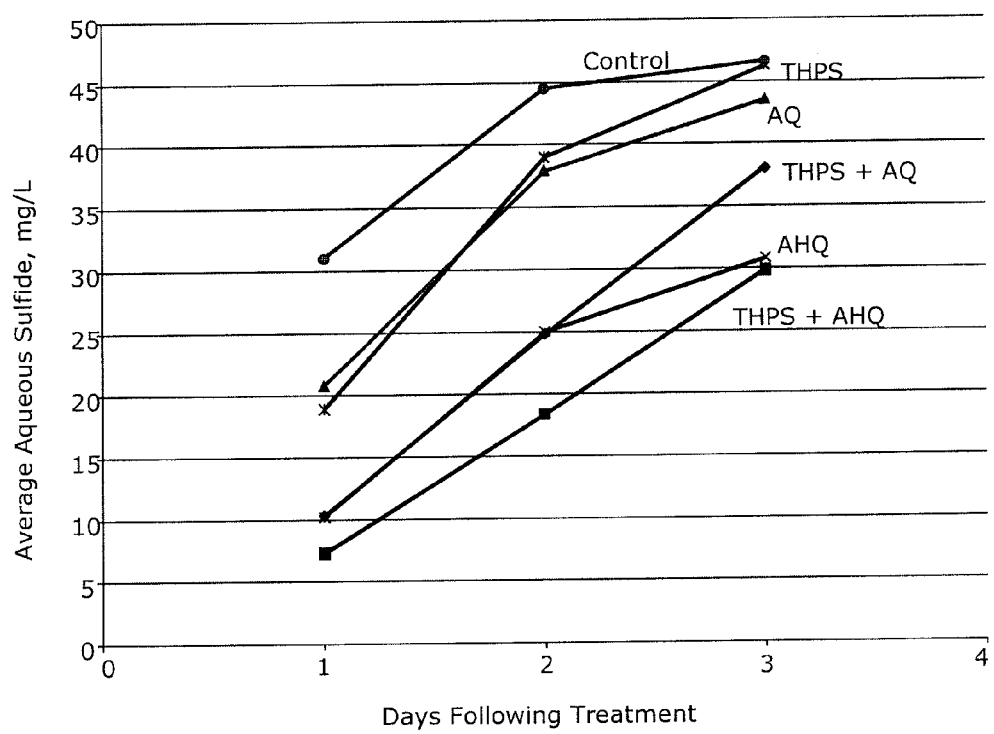
FIG. 1 is a graph of the effects of various compositions on average aqueous sulfide content in tubes of biofilms on granite chips over time. THPS—tetrakishydroxymethylphosphonium sulfate; AQ—anthraquinone; AHQ—anthrahydroquinone; Control—no treatment.

One method for controlling the production of $H_2S$ in tanks, pipes, and other vessels is a dual treatment of adding anthrahydroquinone (AHQ), a biostat, to inhibit production of $H_2S$ by the sulfate-reducing bacteria and separately adding a biocide, to kill the bacteria, as described, for example in Burger, et al., *SPE Projects, Facilities & Construction* 2: 1-9, 2007. Appropriate biocides include, but are not limited to tetrakishydroxymethylphosphonium sulfate (THPS), glutaraldehyde, formaldehyde, acrolein, and cocodiamine. THPS is a preferred biocide.

In this method, AHQ is added to the contents of the vessel as a dialkali salt solution and the THPS is added as a separate solution. This method necessitates storing, shipping, and adding the two components separately, which increases costs. However, because of radical differences in pH, it has not previously been possible to combine stock concentrations of AHQ and THPS solutions into a single product. A very high pH, ≥13, is required to maintain the solubility of AHQ in high concentrations, whereas concentrated solutions of THPS are very acidic, pH≤4. Mixing the THPS solution with the AHQ solution results in an unfavorable exothermic reaction and produces a sticky, insoluble glob.

As described in Example 1, a method has now been developed to prepare a composition containing both AHQ and THPS which obviates the need to store, ship, and add these compounds separately. First, a slurry of AHQ is prepared by acidifying a solution of AHQ di-alkali salt. Slurries with AHQ concentrations up to about 9 weight percent can be prepared. When the pH of the slurry becomes compatible with the pH of the THPS solution, pH≤about 10, the THPS solution is added. Stock solutions of AHQ-THPS can be prepared containing 1-7 wt % AHQ (preferably 3-6 wt % AHQ), and 15-50 wt % THPS (preferably 25-35 wt % THPS). The solution has a pH of 3-9 (preferably 4-7).

Concentrations of AHQ and THPS in the solution can be selected to suit a particular application. In general, a high biocide concentration is used with a low AHQ concentration and vice versa. Preferred stock solutions include (1) 5 wt % AHQ with 30 wt % THPS for use in tank treatments where a high biocide content is necessary to control other problem bacteria, such as acid-producing bacteria, in addition to the sulfate-reducing bacteria; (2) 7 wt % AHQ with 15 wt % THPS for use in tank treatments to control primarily the activity of sulfate-reducing bacteria; and (3) 2.5 wt % AHQ and 50 wt % THPS for use in pipeline systems.

To control sulfide production, the stock solution of AHQ-THPS is added to a vessel or conduit. Vessels include, but are not limited to, water tanks, slop tanks, separators, and free-water knockouts (FWKO). Conduits include, but are not limited to, pipes, pipelines, sewer lines, and heat exchanger tubes. Effective amounts of the solution necessary to control sulfide production and treatment schedules are based on parameters such as the microbiological activity in the system to be treated, surface area of the system to be treated, water flow rate through the system, concentration of the stock solution, and efficacy of treatment. For example, a water tank could be treated with a 7% AHQ/15% biocide stock solution using about 20 L stock solution per 100 $m^2$ of tank cross-sectional area weekly, bi-weekly, or bi-monthly. For solutions with lower AHQ concentrations, e.g., 1% AHQ/50% biocide, up to 140 L of solution could be used per 100 $m^2$ of tank cross-sectional area.

Water tank treatment is intended to deposit the AQ or AHQ particles into the accumulated sediment at the bottom of the tank. SRB grow and form biofilms within this sediment and much of the $H_2S$ biogeneration in tanks occurs within the sediment. In practice, water flowing into the tanks is treated with the AQ or AHQ. The treated water mixes with water in the tank and the AQ or AHQ particles settle to the bottom. However, many of the particles flow out of the tank with the effluent water, decreasing the overall efficacy of the treatment. Therefore, as described below in Example 3, Test Series #3, when treating tanks, it can be more effective to use a composition with a larger particle size, such as an AHQ slurry. Slurry solutions can be prepared containing 1-9 wt % AHQ (preferably 3-6 wt % AHQ). Anthraquinone can be added to the solution to a concentration of 1 to 45 wt %. The solution (with or without anthraquinone) has a pH of 5-9 (preferably 6.5-8). The effective amount of slurry will depend on the size of the vessel or system being treated, the microbiological activity in the system, and the depth of the sediment in the vessel.

The following examples show that the compositions and methods of the invention can be used to improve the efficacy and cost-effectiveness of controlling sulfide biogeneration under different conditions.

Although the invention is illustrated and described with reference to examples and specific embodiments, the invention is not limited to the details shown. Various modifications may be made within the scope and range of equivalents of the claims without departing from the invention.

EXAMPLES

1. Preparation of Test Solutions/Mixtures

A THPS test solution was prepared by diluting a 75 wt % solution of THPS with deionized water to 10 volume %. The resulting solution contained 0.0991 mg THPS/mg solution or 0.103 mg/µL.

An AQ test mixture ("AQ") was prepared by diluting a 50 wt % aqueous slurry of anthraquinone to 5 wt % in deionized water. The aqueous slurry of anthraquinone had been prepared according to Tatnall, (U.S. Pat. No. 5,500,368). About 90% of the anthraquinone particles are less than about 2.2 µm in size and the mixture has a pH of about 7. The resulting test mixture contained 0.025 mg AQ/mg solution, or 0.0254 mg/µL.

An anthrahydroquinone di-alkali salt test solution ("AHQ") was prepared as per the patent of Krackov, U.S. Pat. No. 5,728,898, by reducing AQ with formamidine sulfinic acid in the presence of sodium hydroxide and water, resulting in a solution containing an equivalent AHQ content of 0.0239 mg AHQ/mg solution, or 0.0254 mg/µL.

An AHQ test mixture ("AHQ-slurry-1") was prepared in a nitrogen glove bag by quantitatively adding sufficient 10 wt % HCl to a 14 wt % stock solution of anthrahydroquinone di-alkali salt, forming a bright yellow slurry and eliminating all traces of the deep red color of the stock solution. A small amount of de-aerated water was then added to reduce the resultant AHQ concentration to the desired level. This resulted in a mixture containing 0.0241 mg AHQ/mg slurry, or 0.025 mg/µL. Most of the AHQ particles in the slurry were about 10 µm or less in size.

A second AHQ mixture ("AHQ-slurry-2") was prepared in a nitrogen glove bag by adding concentrated HCl to a 14 wt % stock solution of anthrahydroquinone di-alkali salt, forming a bright yellow slurry and eliminating all traces of the deep red color of the stock solution. The pH of the solution was measured at 9.6. Additional HCl was added until the pH measured 7.18. This neutral yellow slurry, which contained 8.73 wt % AHQ, was further diluted with de-aerated deionized water to prepare a slurry with 0.0245 mg AHQ/mg slurry, or 0.0254 mg/µL. Most of the AHQ particles in the slurry were about 10 µm or less in size.

An AQ-THPS mixture ("AQ-THPS") was prepared by mixing 0.16 g of a 50 wt % aqueous slurry of anthraquinone (as described above), 3.0 g of a 75 wt % THPS solution, and 27 g DI water. The resultant product contained an AQ:THPS ratio of 0.056 g/g. The mixture was allowed to stand for several hours and a layer of AQ settled at the bottom of the container. The AQ was easily re-dispersed with gentle agitation. Most of the AQ particles were about 2.2 µm or less in size.

An AHQ-THPS mixture ("AHQ-THPS") was prepared in a nitrogen glove bag by adding 51.86 g of a 75 wt % THPS solution, pH 4.0, to 25.4 g of a previously prepared AHQ slurry, pH about 3.5, forming a combined product with 50.3 wt % THPS and 1.76 wt % AHQ, or an AHQ:THPS ratio of 0.0350 g/g, and a pH of about 4.0. When allowed to separate, AHQ formed what appeared to be an emulsion floating above the THPS. The two layers were easily re-dispersed with gentle agitation. Most of the AHQ particles in the slurry were about 10 µm or less in size.

AQ-AHQ neutral pH slurries were prepared at AQ:AHQ ratios of 1:1, 2:1, and 4:1 by mixing appropriate amounts of a 50 wt % AQ slurry (as described above) and AHQ-slurry-2, pH 7.18, containing 8.73 wt % AHQ. These slurries were diluted to test mixtures, each containing a combined 10 wt % AQ plus AHQ, by adding the slurries to de-aerated DI water.

The final mixtures contained 0.105, 0.019, and 0.026 mg AQ+AHQ per mg mixture for the 1:1, 2:1, and 4:1 ratios, respectively. Most of the AHQ particles in the slurry were about 10 µm or less in size and most AQ particles were about 2.2 µm or less in size.

2. Procedure for Evaluation

The following procedure was used to evaluate the efficacy of each solution:

1. Load 7 grams of crushed granite chips into 15-ml culture tubes; autoclave.

2. Prepare an inoculum by adding a culture of Prudhoe Bay sulfate reducing bacteria to a flask containing an appropriate iron-free culture medium for sulfate reducing bacteria that further contains 90% deaerated artificial sea water. Incubate bacteria anaerobically at 30° C. for 3-4 days.

3. Fill each 15 ml culture tube containing granite chips with the inoculum; incubate tubes anaerobically at 30° C. for 7-11 days in a Lab-Line Orbit Environ-Shaker set at 30° C. and 120 rpm. All incubation steps for the bacteria in the culture tubes were performed is in the Environ-Shaker.

4. Pour off spent medium and fill with fresh medium. Incubate for 6-7 days then replace medium with fresh medium again. Repeat medium change after 4-8 days and incubate for 3-5 additional days.

5. Treat the biofilms that have grown on the granite chips as described below. Incubate at 30° C.

6. Monitor the aqueous sulfide content in the tubes daily for up to three days, beginning the day after treatment, to determine the effectiveness of each treatment option on generation of hydrogen sulfide. Sulfide dissolved in the medium was determined in mg/L using Hach Method 8131 for the Hach DR-2010 spectrophotometer. The method utilizes methylene blue to measure total sulfides. The sulfide level in each tube was determined by gently inverting the tube several times, uncapping the tube and quickly removing a 125 µl aliquot of solution, and recapping the tube. The aliquot was diluted in 24.9 ml of deionized water in a quartz cuvette for the Hach procedure. The procedure is summarized in Table 1 for three separate test series.

TABLE 1

Preparation and Treatment Schedule

| | Day Number | | |
|---|---|---|---|
| Procedure | Series #1 | Series #2 | Series #3 |
| 2. Prepare Inoculum | 0 | 0 | 0 |
| 3. Fill tubes | 3 | 4 | 4 |
| 4. 1st medium refill | 14 | 14 | 11 |
| 2nd medium refill | 21 | 20 | 18 |
| 3rd medium refill | 25 | 28 | 22 |
| 4th medium refill | — | — | 29 |
| 5. Treatments | 31 | 33 | 25 |
| | | | 27 |
| 6. Monitor | 32, 33, 34 | 34, 35, 36 | 26, 27 28, 29 |

3. Inhibition of H2S Biogeneration from Biofilms by Test Solutions

Test Series #1

Following the growth of the sulfate reducing bacteria (SRB) biofilms on the granite chips in the culture tubes, the biofilms were treated by injecting the appropriate test solution and then gently tumbling the tubes for two minutes on a Barnstead/Thermolyne Labquake Tube Shaker to allow the treatment solution to dynamically contact the biofilms.

Test compound solutions were injected into the tubes. THPS was added to 51 ppmw per tube. AQ and AHQ-slurry-1 were added to 25 ppmw AQ or AHQ per tube. Each tube contained about 14 ml of medium. The tubes were tumbled for two minutes, then moved to a nitrogen glove bag. The liquid was removed and the tubes were washed once with is medium and then refilled with medium. The tubes were then tumbled once more for two minutes before being placed in a Lab-Line Orbit Environ-Shaker set at 30° C. and 120 rpm for incubation.

Control tubes contained biofilms on granite chips and culture medium, but no test compound. Control tubes were otherwise handled as described above for test-compound tubes.

In THPS-treated tubes all of the residual THPS was removed so that biocidal activity occurred only during the contact time while tumbling. In AQ and AHQ treated tubes, residual test solutions were allowed to remain in the tubes to simulate treatment in a tank, where AQ or AHQ settles in the biofilm/sludge at the bottom of the vessel. Treatments were performed in duplicate.

Results are presented in Table 2 and FIG. 1. These results demonstrate that AHQ is superior to AQ at inhibiting $H_2S$ biogeneration from SRB biofilms. THPS treatment was designed to have only a minor biocidal effect on the biofilm in order to allow a definitive impact of AQ or AHQ. AQ administered alone was comparable to THPS treatment. The combination of THPS plus AQ treatment was more effective than either substance alone. AHQ was superior to THPS, AQ, and the combination of THPS and AQ at inhibiting $H_2S$ generation. At three days of treatment the combination of THPS plus AHQ showed similar efficacy to AHQ alone.

TABLE 2

Treatments and Sulfide Monitoring Results

| | | | Sulfides | | |
|---|---|---|---|---|---|
| Tube | Soln | µL | Day 1 | Day 2 | Day 3 |
| 13 | THPS + AQ | 7 + 13.8 | 11 | 22.8 | 38 |
| 14 | THPS + AQ | 7 + 13.8 | 9.6 | 26.8 | 38 |
| 15 | THPS + AHQ | 7 + 14 | 7.2 | 16.8 | 27.8 |
| 16 | THPS + AHQ | 7 + 14 | 7.4 | 20 | 31.8 |
| 17 | AQ | | 13.8 | 22.6 | 41.2 | 46.2 |
| 18 | AQ | | 13.8 | 19 | 34.6 | 40.8 |
| 19 | AHQ | | 14 | 9.2 | 23 | 30.6 |
| 20 | AHQ | | 14 | 11.2 | 27 | 31 |
| 21 | THPS | | 7 | 18 | 39.6 | 46.2 |
| 22 | THPS | | 7 | 19.8 | 38.4 | 46.2 |
| 23 | Control | | 0 | 32.2 | 46.8 | 46.6 |
| 24 | Control | | 0 | 29.8 | 42.2 | 46.6 |

Test Series #2

This test series was performed to further compare the efficacy of slurries of AHQ and AQ and combinations of AHQ/AQ in slurries in controlling $H_2S$ emissions. AHQ-slurry-2 was used in this series of experiments. The tests were performed by first removing the spent medium from the tubes, refilling with fresh medium, treating with the test solution, tumbling the tubes for two minutes, and then incubating at 30° C. in the Lab-Line Orbit Environ-Shaker.

Figure 2:
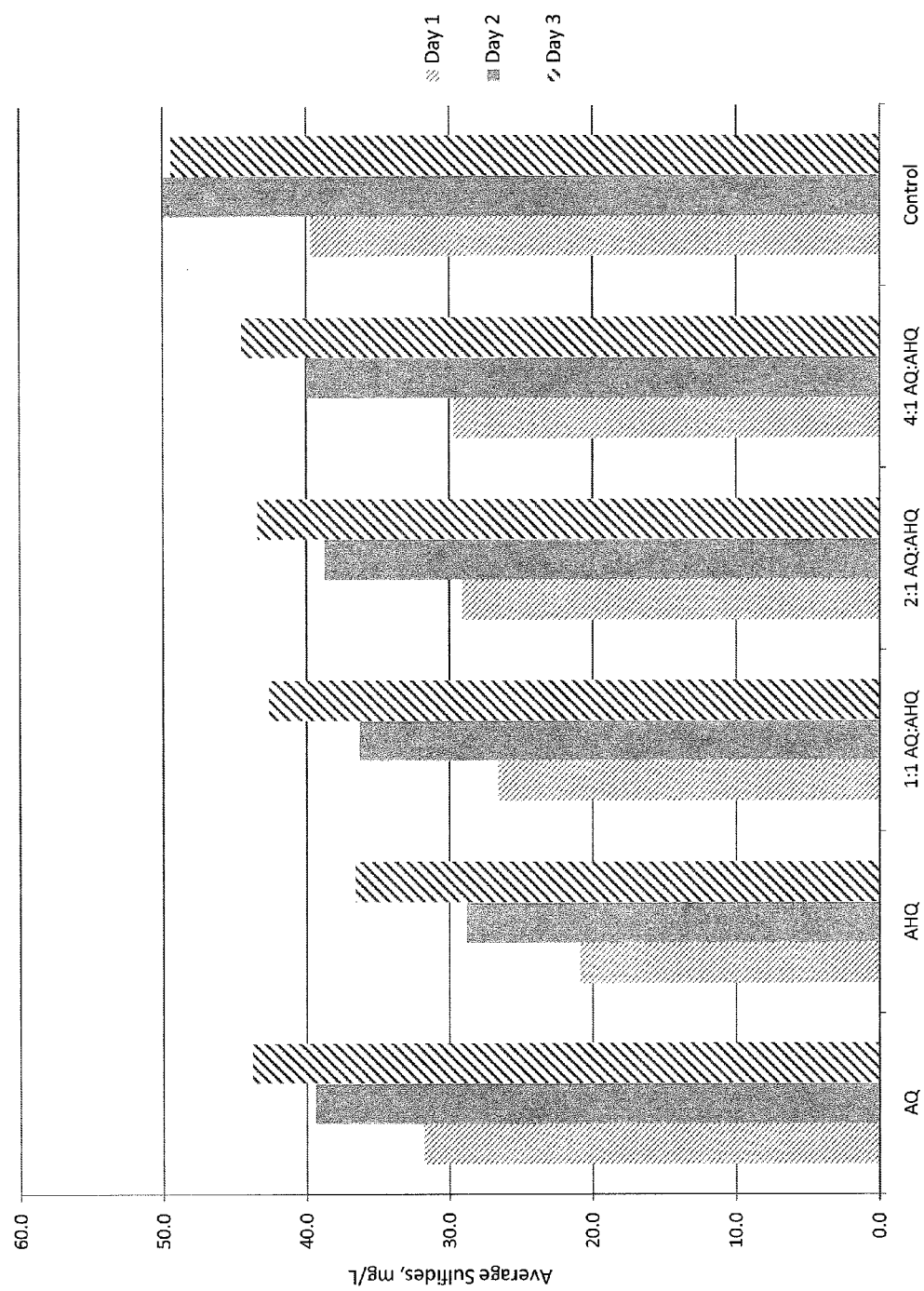
FIG. 2 is a graph of the effects of different combinations of AQ and AHQ neutral slurries on sulfide reduction.

Treatments were made with AQ, AHQ, and combination slurries as summarized in Table 3. Each test was made with the same combined mass of active AQ plus AHQ. Results, as summarized in Table 3 and FIG. 2, confirmed the results of Series #1 in that all treatments were effective compared with the control. AHQ solution alone was more effective than AQ solution alone or AHQ/AQ neutral slurry combinations at inhibiting the generation of $H_2S$.

TABLE 3

Treatments and Sulfide Monitoring Results for Test Series #2

| Tube | Treatment | uL | Sulfides, mg/L | | |
|------|-----------|------|--------|--------|--------|
|      |           |      | Day 1  | Day 2  | Day 3  |
| 1    | AQ        | 13.8 | 33.2   | 40     | 44.4   |
| 2    | AQ        | 13.8 | 30.4   | 38.8   | 43.2   |
| 3    | AHQ       | 13.8 | 22.2   | 31     | 36.8   |
| 4    | AHQ       | 13.8 | 19.6   | 26.6   | 36.4   |
| 5    | 1:1 AQ:AHQ | 23.3 | 25    | 34.8   | 42.6   |
| 6    | 1:1 AQ:AHQ | 23.3 | 28.2  | 37.8   | 42.6   |
| 7    | 2:1 AQ:AHQ | 18.2 | 30    | 39.2   | 45.4   |
| 8    | 2:1 AQ:AHQ | 18.2 | 28.2  | 38.2   | 41.4   |
| 9    | 4:1 AQ:AHQ | 13.8 | 29.2  | 39.2   | 44.6   |
| 10   | 4:1 AQ:AHQ | 13.8 | 30.2  | 40.8   | 44.4   |
| 11   | Control   | 0.0  | 40.4   | 51.6   | 50     |
| 12   | Control   | 0.0  | 39     | 48.4   | 48.8   |

Test Series #3

Experiments performed comparing AHQ di-alkali salt solution to AHQ-slurry-2 using the procedure described in Test Series #2 showed that the AHQ di-alkali salt solution was superior to AHQ neutral slurry in reducing sulfides. Each test treatment contained 18 ppmw AHQ. On day 3 of treatment, sulfides for AHQ-slurry-2 treatment were 31.8 mg/L, whereas sulfides for AHQ di-alkali salt solution treatment were 7.4 mg/L. This result may be due to the smaller, submicron size of the AHQ particles that form upon the addition of the anthrahydroquinone di-alkali salt solution into the medium (Burger, et al., *SPE Projects, Facilities & Construction* 2: 1-9, 2007). However, under some circumstances, larger particle sizes are preferable. Test series #3 was performed with a different procedure to simulate the effect of gravity settling of the AQ and AHQ particles during treatments in tanks.

Gravity settling in the tank was simulated by spinning the culture tubes after treatment in a laboratory centrifuge at 2000 to 2700 rpm. The AQ or AHQ particles then "settled" to the bottom of the tube and were able to deposit into the biofilm on the granite chips. The medium above the granite chips was then removed and replaced with fresh medium. The tubes were then incubated at 30° C. in the Lab-Line Orbit Environ-Shaker. The concentration of AQ or AHQ in the removed medium was analyzed to determine the amount of AQ or AHQ deposited in the biofilm. Experiments were run with duplicate samples.

Two series of tests were performed with this procedure. Series #3a compared the efficacy of treating with the AHQ di-alkali salt test solution (AHQ) and the AHQ test mixture #2 (AHQ-slurry-2) at the same AHQ mass loading (0.254 mg AHQ). Two different centrifugation times (20 sec, 60 sec) were utilized in Test Series #3a to represent two different tank residence times.

The results of test series #3a are summarized in Table 4. AHQ-slurry-2 was almost twice as effective as AHQ at inhibiting $H_2S$ generation, regardless of the centrifugation time.

These results also show that more of the AHQ particles from AHQ-slurry-2 deposited in the biofilm on the granite chips than those from AHQ, making the AHQ-slurry-2 more effective in treating a simulated tank. Although the larger particles in AHQ slurries are less effective than the much smaller particles of the AHQ di-alkali salt solution at inhibiting $H_2S$ generation on a per unit weight basis, AHQ-slurry-2 is more effective in simulated tank is treatment because more particles are deposited in the biofilm sediment due to their larger size. This property also makes the slurry composition more cost-effective for tank treatment.

TABLE 4

Results from test series 3a

| Tube | Treatment | Time, sec | Sulfides, mg/L | | | % AHQ Deposited |
|------|-----------|-----------|------|------|------|------|
|      |           |           | Day 1 | Day 2 | Day 3 |      |
| 1 | AHQ, dialkali salt solution | 60 | 36.6 | 50.8 | 53.6 | 36 |
| 2 | AHQ, dialkali salt solution | 60 | 21.8 | 37 | 42.6 | 38 |
| 3 | AHQ-slurry-2 | 60 | 18.2 | Tube broke | | 60 |
| 4 | AHQ-slurry-2 | 60 | 15.8 | 26.2 | 31 | 89 |
| 5 | AHQ, dialkali salt solution | 20 | 29 | 37.6 | 42 | 30 |
| 6 | AHQ, dialkali salt solution | 20 | 31 | 45.2 | 48.6 | 33 |
| 7 | AHQ-slurry-2 | 20 | 13.6 | 22.4 | 25.8 | 86 |
| 8 | AHQ-slurry-2 | 20 | 14 | 18 | 20.6 | 88 |

Test Series #3b was performed with the same procedure as Test Series #3a to compare the efficacy of the AQ test mixture (AQ) with that of AHQ-slurry-2 at the same AHQ or AQ mass loading (0.254 mg). The tubes were spun for 20 seconds. The results, summarized in Table 5, demonstrate that AHQ was superior to AQ in inhibiting $H_2S$ generation.

TABLE 5

Results from Test Series #3b

| Tube | Treatment | Time, sec | Sulfides, mg/L | |
|------|-----------|-----------|-------|-------|
|      |           |           | Day 1 | Day 2 |
| 9  | AHQ-slurry-2 | 20 | 24   | 43.2 |
| 10 | AHQ-slurry-2 | 20 | 26.4 | 42   |
| 11 | AQ        | 20 | 43.8 | 54.2 |
| 12 | AQ        | 20 | 33.8 | 50.2 |
| 13 | Control   | 20 | 38.2 | 52.8 |
| 14 | Control   | 20 | 34.2 | 50.6 |

We claim:

1. An aqueous stock composition for inhibiting sulfide biogeneration from biofilms, the composition comprising an aqueous solution of anthrahydroquinone and tetrakishydroxymethylphosphonium sulfate (THPS), wherein the pH of the composition is less than about 9; and wherein the final concentration of anthrahydroquinone is between about 1 to 7 weight percent and the final concentration of the THPS is between about 15 to 50 weight percent.

2. The composition of claim 1, wherein the composition has a pH between 3.0 and 9.0.

3. The composition of claim 1, wherein the composition further comprises a dispersant, a surfactant, or both.

4. The composition of claim 1, wherein the pH of the composition is between 5.0 and 9.0.

5. The composition of claim 4, wherein the composition further comprises anthraquinone.

6. The composition of claim 5, wherein the concentration of anthraquinone is 1 to 45 weight percent.

7. A method for preparing the composition of claim 1, comprising the steps of:
   a) preparing an aqueous solution of anthrahydroquinone dialkali salt;
   b) reducing the pH of the solution of step a) to less than about 9; and
   c) adding the THPS to the solution of step b);
   wherein the final concentration of anthrahydroquinone is between about 1 to 7 weight percent and the final concentration of the THPS is between about 15 to 50 weight percent.

8. A method for inhibiting sulfide biogeneration from biofilms, the method comprising adding an effective amount of the composition of claim 1 to a vessel or a conduit.

9. The method of claim 8, wherein the vessel or conduit contains a biofilm.

* * * * *